(12) United States Patent
Guo et al.

(10) Patent No.: US 10,471,485 B2
(45) Date of Patent: Nov. 12, 2019

(54) FIELD INTENSITY COMPENSATION METHOD FOR CONSTRUCTING NON-UNIFORM ELECTRIC FIELD THROUGH AUXILIARY ELECTRODE

(71) Applicant: SHENYANG INSTITUTE OF APPLIED ECOLOGY, CHINESE ACADEMY OF SCIENCES, Shenyang (CN)

(72) Inventors: Shuhai Guo, Shenyang (CN); Bo Wu, Shenyang (CN); Fengmei Li, Shenyang (CN); Sa Wang, Shenyang (CN)

(73) Assignee: SHENYANG INSTITUTE OF APPLIED ECOLOGY, CHINESE ACADEMY OF SCIENCES, Shenyang, Liaoning (CN)

(*) Notice: Subject to any disclaimer, the term of this patent is extended or adjusted under 35 U.S.C. 154(b) by 239 days.

(21) Appl. No.: 15/532,762

(22) PCT Filed: Mar. 30, 2016

(86) PCT No.: PCT/CN2016/077778
§ 371 (c)(1),
(2) Date: Jun. 2, 2017

(87) PCT Pub. No.: WO2017/152439
PCT Pub. Date: Sep. 14, 2017

(65) Prior Publication Data
US 2018/0043405 A1  Feb. 15, 2018

(30) Foreign Application Priority Data
Mar. 11, 2016 (CN) .......................... 2016 1 0144173

(51) Int. Cl.
*B09C 1/00* (2006.01)
*B09C 1/08* (2006.01)
(Continued)

(52) U.S. Cl.
CPC ............... *B09C 1/085* (2013.01); *B09C 1/00* (2013.01); *B09C 1/08* (2013.01); *A01N 25/00* (2013.01);
(Continued)

(58) Field of Classification Search
USPC .......................................... 405/128.4, 128.7
See application file for complete search history.

(56) References Cited

U.S. PATENT DOCUMENTS 4,124,359 A * 11/1978 Geller ....................... B03C 3/40
96/65
5,545,803 A  8/1996 Heath et al.
(Continued)

FOREIGN PATENT DOCUMENTS

CN  1695835 A   11/2005
CN  101767105 A   7/2010
(Continued)

OTHER PUBLICATIONS

Chinese Search Report dated Feb. 6, 2018 for CN Application No. 201610144173 (1 page).
(Continued)

*Primary Examiner* — Danny Nguyen
(74) *Attorney, Agent, or Firm* — Smith, Gambrell & Russell, LLP

(57) ABSTRACT

Presented is an electric field intensity compensation method for constructing a non-uniform electric field through an auxiliary electrode, including steps of: in a matrix electrode unit, designing an auxiliary electrode arrangement position according to the spatial distribution of the pollutant concentration; designing the polarity of the auxiliary electrode according to the position relationship between the auxiliary electrode and matrix electrodes; and constructing a non-uniform electric field by the auxiliary electrode and the (Continued)

matrix electrodes to implement space compensation of the electric field intensity. In the present invention, a non-uniform electric field matching a pollutant concentration field is constructed by setting the space arrangement and polarity of the auxiliary electrodes on the basis of the matrix electrodes according to the spatial distribution of the pollutant concentration, the contradiction of consistency between the heterogeneity of the spatial distribution of the pollutants and the removal efficiency of the uniform electric field is solved, and the spatial difference of efficiency of electrokinetically remedying organic contaminated soil is avoided, thereby improving the overall space remediation efficiency of electrokinetic remediation.

4 Claims, 1 Drawing Sheet

(51) Int. Cl.
  *B09C 1/10* (2006.01)
  *A01N 25/00* (2006.01)
  *A01N 63/02* (2006.01)
  *C05G 3/04* (2006.01)

(52) U.S. Cl.
  CPC .............. *A01N 63/02* (2013.01); *B09C 1/10* (2013.01); *C05G 3/04* (2013.01)

(56) References Cited

U.S. PATENT DOCUMENTS

| | | | |
|---|---|---|---|
| 5,846,393 A | 12/1998 | Clarke et al. | |
| 5,865,964 A | 2/1999 | Clarke et al. | |
| 6,145,244 A * | 11/2000 | Hodko | A01B 47/00 210/602 |
| 6,193,867 B1 | 2/2001 | Hitchens | |
| 9,162,264 B2 | 10/2015 | Guo et al. | |
| 2018/0043406 A1 | 2/2018 | Guo et al. | |

FOREIGN PATENT DOCUMENTS

| | | |
|---|---|---|
| CN | 102294350 A | 12/2011 |
| CN | 203253713 U | 10/2013 |
| CN | 104550216 A | 4/2015 |
| CN | 104550217 A | 4/2015 |
| CN | 104646403 A | 5/2015 |
| CN | 105290104 A | 2/2016 |
| CN | 105312308 A | 2/2016 |
| JP | 2006-346549 A | 12/2006 |

OTHER PUBLICATIONS

Chinese Office Action dated Feb. 26, 2018 for CN Application No. 201610144173 (5 pages in Chinese with English Translation).

International Search Report dated Dec. 15, 2016 for International Patent Application No. PCT/CN2016/077778 (4 pages in Chinese with English translation).

Written Opinion dated Dec. 15, 2016 for International Patent Application No. PCT/CN2016/077778 (3 pages in Chinese with English translation).

International Preliminary Report on Patentability dated Sep. 11, 2018 for International Patent Application No. PCT/CN2016/077778 (4 pages in Chinese with English translation).

Li, Ting-ting, et al. Effect of Periodic Switching Electrode Polarity on Electro-Bioremediation of Oil Contaminated Soil. China Academic Journal Electronic Publishing House. Environmental Engineering: Soil Remediation. 2015. pp. 154 and 159-163 (in Chinese with English abstract and machine translation).

* cited by examiner

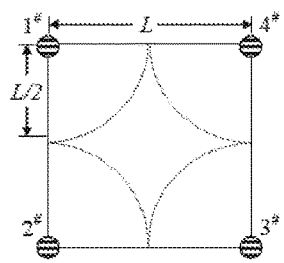
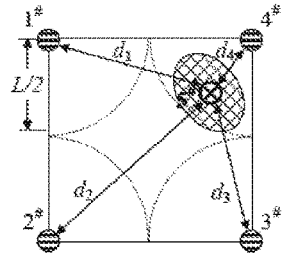
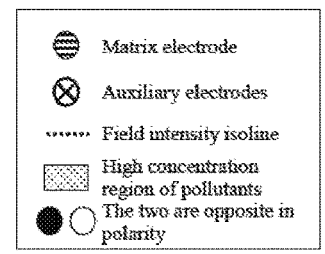
Figure 1-1　　　　Figure 1-2
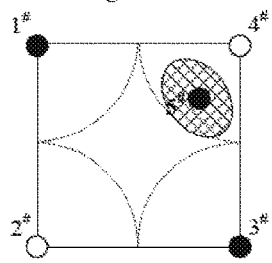
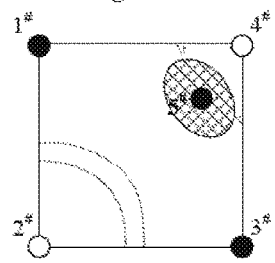
Figure 1-3　　　　Figure 1-4
Figure 1
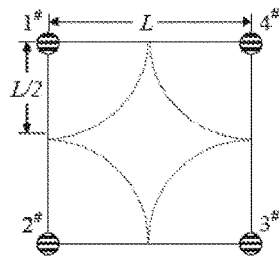
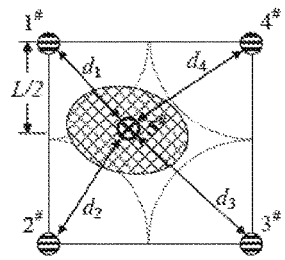
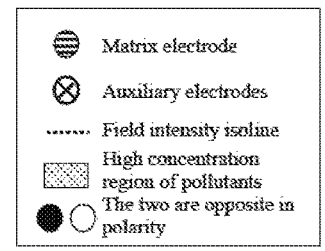
Figure 2-1　　　　Figure 2-2
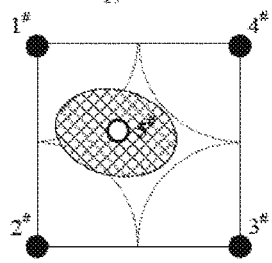
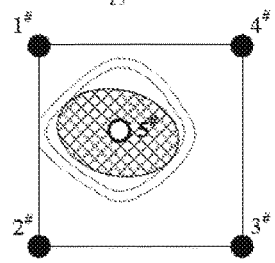
Figure 2-3　　　　Figure 2-4
Figure 2

FIELD INTENSITY COMPENSATION METHOD FOR CONSTRUCTING NON-UNIFORM ELECTRIC FIELD THROUGH AUXILIARY ELECTRODE

TECHNICAL FIELD

The present invention relates to a technology for the remediation of organic contaminated soil, particularly to a field intensity compensation method for constructing a non-uniform electric field through an auxiliary electrode.

BACKGROUND

Electrokinetic remediation is an emerging technology for the remediation of organic contaminated soil. In the existing electrokinetic remediation process, paired electrodes are inserted into contaminated soil, and a weak direct current is applied to form an electric field. Under the combined action of electrochemical reactions and electrokinetic effects, organic pollutants in soil are effectively removed.

In the previous study process, M×N matrix electrodes are arranged in an iso-spacing grid, and by the periodic polarity switching between the positive electrode and the negative electrode, a uniform electric field implementing full coverage is formed (CN 102294350 B). However, since the spatial distribution of the concentration of the organic pollutants in soil has heterogeneity, and the degradation efficiency is related to the electric field intensity, great spatial variability of the residual amount after pollutant remediation will be caused under the condition of the uniform electric field, so that the overall remediation efficiency of organic contaminated soil cannot reach a set standard.

Therefore, regarding to the contradiction of consistency between the heterogeneity of the spatial distribution of the organic pollutants in soil and the removal efficiency of the uniform electric field, the method of constructing the non-uniform electric field by additionally setting auxiliary electrodes, setting the polarity and switching mode in the high pollutant concentration region can compensate the electric field intensity of the high pollutant concentration region, thereby avoiding the spatial difference of efficiency of electrokinetically remedying organic contaminated soil, and having great significance to improve the overall efficiency of electrokineticaliy remedying organic contaminated soil.

SUMMARY

The purpose of the present invention is to provide an electric field intensity compensation method for constructing a non-uniform electric field through an auxiliary electrode.

To realize the above-mentioned purposes, the present invention discloses the technical solution: an electric field intensity compensation method for constructing a non-uniform electric field through an auxiliary electrode, comprising the following steps:

in a matrix electrode unit, determining auxiliary electrode layout positions according to the spatial distribution of the pollutant concentration, and inserting auxiliary electrodes;

controlling the polarity of the auxiliary electrodes according to the position relationship between the auxiliary electrodes and matrix electrodes;

constructing a non-uniform electric field by the auxiliary electrode and the matrix electrodes to implement space compensation.

The step of determining the auxiliary electrode layout positions according to the spatial distribution of the pollutant concentration comprises the following steps:

taking adjacent 4 matrix electrodes as a unit, wherein when a region of which the pollutant concentration is higher than a threshold is present in the matrix electrode unit, the geometric center position of the region is an auxiliary electrode layout position.

The step of controlling the polarity of the auxiliary electrodes according to the position relationship between the auxiliary electrodes and matrix electrodes comprises the following steps:

$d_i$ is the distance between an auxiliary electrode and the $i^{th}$ matrix electrode, where n=4; the distance between the field intensity E corresponding to the average removal rate of pollutants and the closest matrix electrode is R;

when $$\prod_{i=1}^{n} (d_i - R) \leq 0,$$

the polarity of adjacent matrix electrodes is made to be opposite, and the polarity of the auxiliary electrode is opposite to that of the matrix electrode closest to same;

when $$\prod_{i=1}^{n} (d_i - R) > 0,$$

the polarity of matrix electrodes is made to be identical, and the polarity of the auxiliary electrode is opposite to that of the matrix electrode.

The step of constructing the non-uniform electric field by the auxiliary electrodes and matrix electrodes specifically comprises the steps of: constructing the non-uniform electric field by switching between the positive electrode and the negative electrode through the polarity of the auxiliary electrodes and the polarity of the matrix electrodes.

The present invention has the following advantages and beneficial effects:

In the present invention, a non-uniform electric field matching a pollutant concentration field is constructed by setting the space arrangement and polarity of the auxiliary electrodes on the basis of the matrix electrodes according to the spatial distribution of the pollutant concentration, the effective compensation of the field intensity in the high concentration region of pollutants is implemented, the contradiction of consistency between the heterogeneity of the spatial distribution of the pollutants and the removal efficiency of the uniform electric field is solved, and the spatial difference of efficiency of electrokinetically remedying organic contaminated soil is avoided, thereby improving the overall space remediation efficiency of electrokinetic remediation.

DESCRIPTION OF THE DRAWINGS

FIG. 1 is a diagram showing an auxiliary electrode position, polarity switching and non-uniform electric field of embodiment 1;

wherein FIG. 1-1 is a schematic diagram showing a matrix electrode layout and field intensity isoline of embodiment 1;

FIG. 1-2 is a schematic diagram showing an auxiliary electrode layout position of embodiment 1;

FIG. 1-3 is a schematic diagram showing the polarity switching between an auxiliary electrode and a matrix electrode of embodiment 1;

FIG. 1-4 is a schematic diagram showing the non-uniform electric field of embodiment 1;

FIG. 2 is a diagram showing an auxiliary electrode position, polarity switching and non-uniform electric field of embodiment 2;

wherein FIG. 2-1 is a schematic diagram showing a matrix electrode layout and field intensity isoline of embodiment 2;

FIG. 2-2 is a schematic diagram showing an auxiliary electrode layout position of embodiment 2;

FIG. 2-3 is a schematic diagram showing the polarity switching between an auxiliary electrode and a matrix electrode of embodiment 2;

FIG. 2-4 is a schematic diagram showing the non-uniform electric field of embodiment 2.

DETAILED DESCRIPTION

The present invention will be further described in detail below in combination with the drawings and the embodiments.

An electric field intensity compensation method for constructing a non-uniform electric field through an auxiliary electrode, comprising the following steps:

(1) in a matrix electrode unit, designing auxiliary electrode layout positions according to the spatial distribution of the pollutant concentration;

(2) designing the polarity of the auxiliary electrodes according to the position relationship between the auxiliary electrodes and matrix electrodes;

(3) constructing a non-uniform electric field by the auxiliary electrode and the matrix electrodes to implement space compensation.

The step of designing the auxiliary electrode layout position specifically comprises:

(1) adjacent 4 matrix electrodes are taken as a unit, wherein the distance between two adjacent matrix electrodes is L;

(2) when a high concentration region of pollutants is presented in the matrix electrode unit, the geometric center position of the high concentration region is an auxiliary electrode layout position;

(3) if no high concentration region of pollutants is presented in the matrix electrode unit, auxiliary electrodes are not laid.

The polarity of the auxiliary electrode is specifically designed as:

(1) the distance between the auxiliary electrode and the matrix electrode is d, and the polarity discrimination distance R of the auxiliary electrode is determined by the field intensity E corresponding to the average removal rate of pollutants;

(2) when $$\prod_{i=1}^{n}(d_i - R) \le 0 \ (n = 4),$$

supposing the polarity of adjacent matrix electrodes are opposite, the polarity of the auxiliary electrode is opposite to that of the matrix electrode closest to same, where $d_i$ is the distance between an auxiliary electrode and the $i^{th}$ matrix electrode;

(3) when $$\prod_{i=1}^{n}(d_i - R) > 0 \ (n = 4),$$

supposing the polarity of adjacent matrix electrodes are identical, the polarity of the auxiliary electrode is opposite to that of the matrix electrode;

The non-uniform electric field is specifically constructed as follows:

(1) the non-uniform electric field is constructed by switching between the positive electrode and the negative electrode through the polarity of the auxiliary electrodes and the polarity of the matrix electrodes according to the auxiliary electrode layout position and the polarity design of the auxiliary electrode;

(2) the field intensity distribution of the non-uniform electric field is essentially consistent with the field distribution of the pollutant concentration, thereby effectively reducing the spatial variability of the pollutant concentration.

The spatial distribution of the pollutant concentration is specifically formed as follows:

(1) continuous distribution of spatial concentration of pollutants is formed by grid sampling and measuring the concentration of pollutants of a sampling point by using a Kriging spatial interpolation;

(2) by taking the sum of the mean value μ of the concentration of pollutants and the standard deviation δ as a threshold, the spatial distribution of the concentration of pollutants is divided into a high concentration region and a low concentration region.

Embodiment 1

The contaminated soil remedied in this embodiment is petroleum-contaminated soil configured for the laboratory; the collected soil is clay in which visible impurities and roots of grass and trees are removed and which is air-dried naturally and then sieved using a sieve of 2 mm; petroleum is extracted from a certain petroleum pit of Shuguang Oil Production Plant, Liaohe Oil Field Company; petroleum-contaminated soil of 40 g/kg-50 g/kg is non-uniformly prepared, and is air-dried naturally for 7 days; after petroleum is uniformly mixed with soil, the moisture content is adjusted to be 25% using deionized water, and the mixture is filled in an electrokinetic remediation reaction tank (length 20 cm×width 20 cm×height 15 cm).

The spatial distribution of the concentration of petroleum pollutants is implemented as follows: 25 samples (5×5) are collected in total in the reaction tank through the grid distribution point method. By using infrared spectrophotometry, the concentration of petroleum pollutants is measured to have a mean value of oil content μ=44.5 g/kg, a standard deviation δ=7.2 g/kg, and a spatial variation coefficient CV=16.2%. By taking the sum of the mean value of the concentration of pollutants and the standard deviation as a threshold, i.e. by taking μ+δ=51.7 g/kg as a threshold, the spatial distribution of the concentration of pollutants is divided into a high concentration region and a low concentration region, wherein the high concentration region accounts for 10.1% of the total area, and the low concentration region accounts for 89.9% of the total area.

As shown in FIG. 1-1, the matrix electrodes are arranged in a 2×2 matrix, the matrix electrodes are electrodes with the serial number of $1^\#$-$4^\#$ respectively, and the electrode spacing L is 20 cm. The external voltage is 36V and the uniform electric field intensity formed by the matrix electrodes is greater than or equal to 0.8V/cm. Both the auxiliary electrode and the matrix electrodes are made of graphite electrodes (1 cm in diameter, and 20 cm in height), and the external voltage is also 36V.

The field intensity compensation method for constructing a non-uniform electric field through an auxiliary electrode in this embodiment specifically comprises the steps of: 1) designing the arrangement position of the auxiliary electrode according to the spatial distribution of pollutant concentration; 2) designing the polarity of the auxiliary electrode according to the position relationship between the auxiliary electrode and the matrix electrodes; and 3) constructing a non-uniform electric field by the auxiliary electrode and the matrix electrodes, to implement the space compensation of the electric field intensity.

Step 1. The auxiliary electrode arrangement position is specifically designed as follow; is:

As shown in FIGS. 1-1 to 1-2 in FIG. 1, in the uniform electric field formed by four matrix electrodes, the geometric center position of the high concentration region of petroleum pollutants is the arrangement position of the auxiliary electrode ($5^\#$ electrode).

Step 2. The auxiliary electrode polarity is specifically designed as follows:

The previous research result indicates that for the petroleum pollutants, under the electrokinetic remediation condition, the pollutant removal rate is in negative correlation with the electrode distance in space, and the field intensity is also in negative correlation with the electrode distance in space. Therefore, the average removal rate of pollutants in space and corresponding field intensity values can form a set of isolines.

In this embodiment, the field intensity E corresponding to the average removal rate of petroleum pollutants is 1.0V/cm, as shown in FIG. 1-1, and a set of isolines taking the matrix electrode as a centre and having a radius of R=L/2 are formed.

Since the relationship of distance (d) between the auxiliary electrode and the matrix electrodes meets $$\prod_{i=1}^{n} (d_i - R) \leq 0 \ (n = 4),$$

as shown in FIG. 1-3, supposing that the polarity of adjacent matrix electrodes are opposite, the polarity of the auxiliary electrode is opposite to that of the matrix electrodes closest to same, that is, the polarity of $1^\#$ electrode, $3^\#$ electrode and $5^\#$ electrode are identical, the polarity of $2^\#$ electrode and $4^\#$ electrode are identical, and the polarity of $1^\#$ electrode, $3^\#$ electrode and $5^\#$ electrode are opposite to that of $2^\#$ electrode and $4^\#$ electrode.

Step 3. The non-uniform electric field is specifically constructed as follows:

The polarity of the auxiliary electrode and matrix electrodes can be adjusted by a polarity switching controller. As shown in FIG. 1-3, by keeping the polarity switching between the auxiliary electrode and the matrix electrodes, the non-uniform electric field matching the pollutant concentration field is constructed (FIG. 1-4). The time period for polarity switching of electrodes, t=4 h, and the total remediation time T=60 d.

See Table 1 for remediation result.

TABLE 1

| Group | Electrode arrangement | Electric field type | Remediation efficiency (%) | Coefficient of variation of pollutant concentration (%) | Processing time (d) |
|---|---|---|---|---|---|
| Control group | None | None | 2.7% | 16.2 | 60 |
| Experimental group 1 | Matrix electrode | Uniform electric field | 55.7% | 15.2 | 60 |
| Experimental group 2 | Auxiliary electrodes + matrix electrode | Non-uniform electric field | 70.2% | 3.5 | 60 |

Embodiment 2 is different from embodiment 1 in that:

The mean value of the concentration of petroleum pollutants is μ=34.3 g/kg, the standard deviation δ=8.8 g/kg, and the spatial variation coefficient CV=25.7%. By taking the sum of the mean value of the concentration of pollutants and the standard deviation as a threshold, i.e. by taking μ+δ=43.1 g/kg as a threshold, the spatial distribution of the concentration of pollutants is divided into a high concentration region and a low concentration region, wherein the high concentration region accounts for 20.7% of the total area, and the low concentration region accounts for 79.3% of the total area.

As shown in FIGS. 2-1 to 2-4 in FIG. 2, in this embodiment, since the relationship of distance between the auxiliary electrode and the matrix electrodes meets $$\prod_{i=1}^{n} (d_i - R) > 0 \ (n = 4),$$

as shown in FIG. 2-3, supposing that the polarity of matrix electrodes are identical, the polarity of the auxiliary electrode is opposite to that of the matrix electrodes, that is, the polarity of $1^\#$ electrode, $2^\#$ electrode, $3^\#$ electrode and $4^\#$ electrode are identical, and the polarity of $1^\#$ electrode, $2^\#$ electrode, $3^\#$ electrode and $4^\#$ electrode are opposite to that of $5^\#$ electrode.

As shown in FIG. 2-3, by keeping the polarity switching between the auxiliary electrode and the matrix electrodes, the non-uniform electric field matching the pollutant concentration field is constructed (FIG. 2-4). See Table 2 for remediation result.

TABLE 2

| Group | Electrode arrangement | Electric field type | Remediation efficiency (%) | Coefficient of variation of pollutant concentration (%) | Processing time (d) |
| --- | --- | --- | --- | --- | --- |
| Control group | None | None | 2.4% | 25.7 | 60 |
| Experimental group 1 | Matrix electrode | Uniform electric field | 53.2% | 19.7 | 60 |
| Experimental group 2 | Auxiliary electrodes + matrix electrode | Non-uniform electric field | 72.7% | 5.8 | 60 |

The above contents are further detailed descriptions of the present invention in combination with specific preferential embodiments. However, it cannot be considered that the specific embodiments of the present invention are only limited to these descriptions. Several simple deductions or replacements may be made without departing from the conception of the present invention, all of which shall be considered to belong to the protection scope of the present invention.

We claim:

1. An electric field intensity compensation method for constructing a non-uniform electric field through an auxiliary electrode, comprising the following steps:
   in a matrix electrode unit, determining an auxiliary electrode layout position according to a spatial distribution of a pollutant concentration, and inserting the auxiliary electrode;
   controlling a polarity of the auxiliary electrode according to the position relationship between the auxiliary electrode and matrix electrodes; and
   constructing the non-uniform electric field by the auxiliary electrode and the matrix electrodes to implement space compensation.

2. The electric field intensity compensation method for constructing a non-uniform electric field through an auxiliary electrode of claim 1, wherein the step of determining the arrangement position of the auxiliary electrode according to the spatial distribution of the pollutant concentration comprises the following steps:
   taking adjacent 4 matrix electrodes as a unit,
   wherein, when a region of which the pollutant concentration is higher than a threshold is present in the matrix electrode unit, the geometric center position of the region is an auxiliary electrode layout position.

3. The electric field intensity compensation method for constructing a non-uniform electric field through an auxiliary electrode of claim 1, wherein the step of controlling the polarity of the auxiliary electrode according to the position relationship between the auxiliary electrode and the matrix electrodes comprises the following steps:
   $d_i$ is the distance between an auxiliary electrode and the $i^{th}$ matrix electrode, where n=4; the distance between the field intensity E corresponding to the average removal rate of pollutants and the closest matrix electrode is R;
   when $$\prod_{i=1}^{n} (d_i - R) \leq 0,$$

the polarity of adjacent matrix electrodes is made to be opposite, and the polarity of the auxiliary electrode is opposite to that of the matrix electrode closest to same;
   when $$\prod_{i=1}^{n} (d_i - R) > 0,$$

the polarity of matrix electrodes is made to be identical, and the polarity of the auxiliary electrode is opposite to that of the matrix electrode.

4. The electric field intensity compensation method for constructing a non-uniform electric field through an auxiliary electrode of claim 1, wherein the step of constructing the non-uniform electric field by the auxiliary electrode and matrix electrodes comprises the steps of: constructing the non-uniform electric field by switching between the positive electrode and the negative electrode through the polarity of the auxiliary electrode and the polarity of the matrix electrodes.

* * * * *